United States Patent
Weber

(10) Patent No.: US 8,647,441 B2
(45) Date of Patent: Feb. 11, 2014

(54) METHOD OF FABRICATING SEMICONDUCTOR CLEANERS

(71) Applicant: Infineon Technologies AG, Neubiberg (DE)

(72) Inventor: Frank Weber, Egmating (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 13/846,595

(22) Filed: Mar. 18, 2013

(65) Prior Publication Data

US 2013/0217232 A1   Aug. 22, 2013

Related U.S. Application Data

(62) Division of application No. 13/408,796, filed on Feb. 29, 2012, now Pat. No. 8,409,363, which is a division of application No. 11/126,424, filed on May 11, 2005, now Pat. No. 8,147,615.

(60) Provisional application No. 60/625,241, filed on Nov. 5, 2004, provisional application No. 60/672,331, filed on Apr. 18, 2005.

(51) Int. Cl.
*B08B 7/02* (2006.01)

(52) U.S. Cl.
USPC ............... 134/16; 15/1; 438/694; 700/266

(58) Field of Classification Search
None
See application file for complete search history.

(56) References Cited

U.S. PATENT DOCUMENTS

| 5,575,859 | A | 11/1996 | Madsen et al. |
| 5,600,134 | A | 2/1997 | Ashe et al. |
| 6,728,641 | B1 | 4/2004 | Cawse |
| 8,147,615 | B2 | 4/2012 | Weber |
| 2003/0063171 | A1 | 4/2003 | Otsuka et al. |
| 2003/0197764 | A1 | 10/2003 | Sato |
| 2004/0077112 | A1 | 4/2004 | Elliott |
| 2012/0160270 | A1 | 6/2012 | Weber |

FOREIGN PATENT DOCUMENTS

| DE | 258495 | A | 7/1988 |
| JP | 56004239 | A | 1/1981 |
| JP | 60133758 | A | 7/1985 |
| JP | 62206858 | A | 9/1987 |
| JP | 63308923 | A | 12/1988 |
| JP | 0304033 | A | 2/1991 |
| JP | 8078814 | A | 3/1996 |

OTHER PUBLICATIONS

Burke, John, "Solubility Parameters: Theory and Application," The Book and Paper Group Annual, vol. 3, 1984, 41 pages.

Sinha, Manish, et al., "Computer Aided Solvent Design for Lithographic Blanket Wash System," Annual AIChE Meeting, Miami, Florida, 1998, 8 pages.

Sinha, Manish, et al., "Systematic Design of Blanket Wash Solvents With Recovery Considerations," Advances in Environmental Research, vol. 5, 2001, pp. 239-249.

Ternet, G.K., et al., "Replacement Solvents for Nonvolatile Residue (NVR) Removal From Painted Space Hardware," Aerospace Report No. TR-2001(8565)-3, Feb. 15, 2001, 23 pages.

*Primary Examiner* — Eric Golightly

(74) *Attorney, Agent, or Firm* — Slater & Matsil, L.L.P.

(57) ABSTRACT

A method of manufacturing cleaning solvents is provided. The method includes selecting a small plurality of test solvents from a large plurality of perspective solvents. The equilibrium composition of a multi-component solution is preferably described by the Hansen solubility model. A small plurality of test solvents is applied to solute samples and the degree of dissolution or swelling recorded. Based on the degree of dissolution or swelling, at least one solvent is selected from the large plurality of perspective solvents based on the Hansen parameters.

19 Claims, 3 Drawing Sheets

METHOD OF FABRICATING SEMICONDUCTOR CLEANERS

This is a divisional application of U.S. application Ser. No. 13/408,796, filed on Feb. 29, 2012 and issued as U.S. Pat. No. 8,409,363 on Apr. 2, 2012 which is a divisional application of U.S. application Ser. No. 11/126,424, filed on May 11, 2005 and issued as U.S. Pat. No. 8,147,615 on Apr. 3, 2012, and which claims the benefit of U.S. Provisional Application No. 60/625,241, filed on Nov. 5, 2004, and U.S. Provisional Application No. 60/672,331, filed on Apr. 18, 2005, all of which applications are hereby incorporated by reference in their entirety.

TECHNICAL FIELD

This invention relates generally to semiconductor device manufacturing and more particularly to a method for fabricating cleaning or stripping solvents for photoresists, dielectrics, processing residues, and other soluble materials.

BACKGROUND

The semiconductor industry uses many cleaning solvents. For example, the manufacture of semiconductor components and integrated circuits is carried out using photolithographic processes. Semiconductor substrates are coated with photoresists, developed, and patterned. After these processes, the photoresist and process residues have to be removed. For this purpose, cleaners, solvents, or strippers are used.

Selection of a cleaner involves considering many factors such as volatility, viscosity, acidity, surface tension, environmental, and health and safety. Another important factor is a cleaner's ability to adequately remove one material while leaving other materials unaffected. A major difficulty facing the user is the bewildering array of cleaners available, but a shortage of information to guide the user in selecting a cleaner that has the desired properties. The difficulty is compounded when proprietary concerns prevent disclosure of the details concerning either the cleaner or the application. Often both the chemical supplier and the semiconductor manufacturer are unwilling to disclose material properties because of the possibility of reverse engineering. For example, a semiconductor manufacturer may be unwilling to disclose the composition of an experimental photoresist or a new low-k dielectric. In situations like this, the cleaner manufacturer can offer little guidance to the user in selecting an appropriate cleaner or other solvent.

Determining the optimum cleaning solvent by trial and error is time consuming and expensive. Product literature and technical reports often include an enormous quantity of data, yet lack the ability to predict whether a solvent will work in a given situation. Thermodynamic phase equilibrium calculations are limited in value by their complexity and lack of suitable equilibrium solubility data, particularly for new materials.

In light of considerations such as these, there remains a need for a method of efficiently selecting or producing cleaning solvents. There is a particular need in manufacturing applications where proprietary concerns prevent disclosure of a solvent or solute composition.

SUMMARY OF THE INVENTION

These and other problems are generally solved or circumvented, and technical advantages are generally achieved, by preferred embodiments of the present invention that provide a method for rapidly selecting a subset of promising cleaners from the universe of available solvents. Once a small group of promising solvents is selected, manufacturers may more effectively allocate scarce resources for determining the optimum solvent (or mixture of solvents) for a given application.

In preferred embodiments, a method of manufacturing cleaning solvents is provided. The cleaning solvents may include a stripping solution for removing a resist or dielectric residue from a semiconductor substrate, for example. A method includes compiling a database that includes solvents and solubility parameters for a large plurality of perspective solvents. The method further includes selecting a small plurality of test solvents from the large plurality of perspective solvents. The small plurality is preferably less than or equal to about 20, and the large plurality is preferably larger than about 200, and more preferably larger than about 20,000. The equilibrium composition of a multi-component solution comprising the solute dissolved in the solvent is preferably described by a predetermined plurality of parameters. The solute may comprise, for example, a material produced in a semiconductor fabrication process.

In preferred embodiments, the plurality of parameters includes Hansen parameters and a Hansen radius of interaction, such as those used in a Hansen solubility model. In preferred embodiments, a small plurality of test solvents is applied to solute samples and the degree of dissolution or swelling recorded. Based on the degree of dissolution or swelling, at least one solvent is selected from the large plurality of perspective solvents based on the Hansen parameters, thereby producing a new cleaning solvent.

In other embodiments, the Hansen solubility model includes additional parameters that enable more accurate solubility predictions. In one embodiment, an additional parameter accounts for oxidizing solution components. In an alternative embodiment, an additional parameter accounts for the acidic/basic property of the solution. Still another embodiment accounts for temperature effects. In still other embodiments, one or more solubility parameters are extended by adjusting at least one of a temperature, a surface tension, a redox potential, an acid content, a viscosity, and a fluoride concentration of the cleaning solvent.

Preferred embodiments provide a method of fabricating a cleaning solvent for removing a residue. Embodiments include calculating a set of solute solubility parameters for the residue by combining the solvent solubility parameters for the test solvents in proportion to the amount of residue dissolved by each member of the small plurality of test solvents. Embodiments may further include mixing at least two solvents from the large plurality of perspective solvents to form a mixture so that the set of solvent solubility parameters for the mixture approximates the set of solute solubility parameters for the residue.

In other embodiments of the invention, calculating the set of solute solubility parameters includes using a surface tension solubility model. Such a model includes constructing a free surface energy plot, calculating a polar free energy and a dispersive free energy of the solute from the surface free energy plot.

Embodiments of the invention may further comprise using the calculated solubility parameters of the cleaning solvent to decide if a formulation is useful to remove a material. Still other embodiments may further comprise using the calculated cleaning parameters of the cleaning solvent to compare different cleaning formulations.

Yet still other alternative embodiments further include an iterative process for fully optimizing the cleaning solvent.

Embodiments further include mixing a plurality of perspective solvents using an equilibrium solubility model based on mole fraction.

Other embodiments of the invention provide a method of fabricating a cleaning solvent for removing a residue. The method includes measuring an amount of the residue dissolved by each member of the small plurality of test solvents, and calculating a set of solute solubility parameters for the residue by combining the solvent solubility parameters for the test solvents in proportion to the amount of residue dissolved by each member of the small plurality of test solvents. Preferably, measuring an amount of the residue dissolved comprises including a non-residue solute adjacent a residue and determining a test solvent selectivity by measuring an amount of non-residue dissolved by the test solvent. Measuring an amount of the residue dissolved may comprise measuring a swelling of the residue.

An embodiment further comprises mixing at least two solvents from the large plurality of perspective solvents to form a mixture so that the set of solvent solubility parameters for the mixture approximates the set of solute solubility parameters for the residue.

Embodiments of the invention may further comprise adjusting at least one of a temperature, a surface tension, a redox potential, an acid content, a viscosity, and a fluoride concentration of the cleaning solvent. The solvent and solute solubility parameters may comprise parameters corresponding to the Hansen solubility model, or an alternative model such as a surface tension model.

In the various embodiments, the cleaning solvent may comprise a photoresist stripper, and the residue comprises a dielectric residue or a resist residue or another material generated or used in a process.

Other embodiments provide a method for fabricating a semiconductor device. The method comprises forming an intermediate semiconductor device on a substrate, wherein the forming includes generating a material to be removed using a cleaning solution. The method further includes fabricating the cleaning solution. Preferably, the fabricating comprises selecting a small plurality of candidate solutions, wherein each member of the small plurality has a known solubility parameter, measuring an amount of swelling caused by each member of the small plurality using a test sample of the material, and calculating a set of solute solubility parameters for the material by combining the solubility parameters for the test solvents in proportion to the amount of the material dissolved by each member of the small plurality of test solvents. Embodiments further comprise selecting a solvent from the large plurality of perspective solvents based on the set of solute solubility parameters for the material, and removing the material using the cleaning solution.

Embodiments may further comprise mixing at least two solvents from the large plurality of perspective solvents to form a mixture so that the set of solubility parameters for the mixture approximates the set of solute solubility parameters for the residue. Other embodiments may further comprise adjusting at least one of a temperature, a surface tension, a redox potential, an acid content, a viscosity, and a fluoride concentration of the cleaning solvent. Calculating the solubility parameters of the cleaning solvent may include a solubility model, such as Hansen or surface tension. In an embodiment, the material to be removed by the cleaning solution comprises a material from a fabrication of a porous dielectric.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

Corresponding numbers and symbols in different figures generally refer to corresponding parts unless otherwise indicated. The figures are drawn to clearly illustrate the relevant aspects of the preferred embodiments and are not necessarily drawn to scale. To more clearly illustrate certain embodiments, a letter indicating variations of the same structure, material, or process step may follow a figure number.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that may be embodied in a wide variety of specific contexts. For example, embodiments of the invention are believed particularly advantageous for fabricating solvents useful in semiconductor manufacturing. The solvents may include cleaners for removing materials such as residues, resists, impurities, reaction byproducts, or unwanted solids.

Preferred embodiments include using equilibrium solubility models known in the chemical arts for predicting what solvent will have the best cleaning properties. One suitable model is the Scatchard-Hildebrand theory of regular solutions. Another is the Flory-Huggins model. The Hansen solubility model is especially preferred.

Sinha, S. and Achenie, L. E. K., "Systematic Design of Blanket Wash Solvents with Recovery Considerations," Advances in Environmental Research (2001), which is hereby incorporated by reference, describe using the Hansen solubility model to select cleaning solvents for the printing industry.

Briefly, the Hansen solubility model includes three parameters that account for dispersion, hydrogen bonding, and polar interactions in solutions. In Hansen's model, the three parameters for the solute and solvent are used calculate a solubility sphere for that solute. A value, known in the chemical arts as an interaction radius, characterizes the size of the sphere. The interaction radius and the three Hansen parameters are a function of the physical properties of the solute. Liquids whose Hansen parameters lie within the solute solubility sphere will dissolve that solute. Since 3D plots are inconvenient to work with, those skilled in the art frequently make a 2D plot by taking a slice of data taken from the solubility sphere. Such a plot, called a Teas plot (named for its developer), is well known in the chemical arts.

Figure 1:
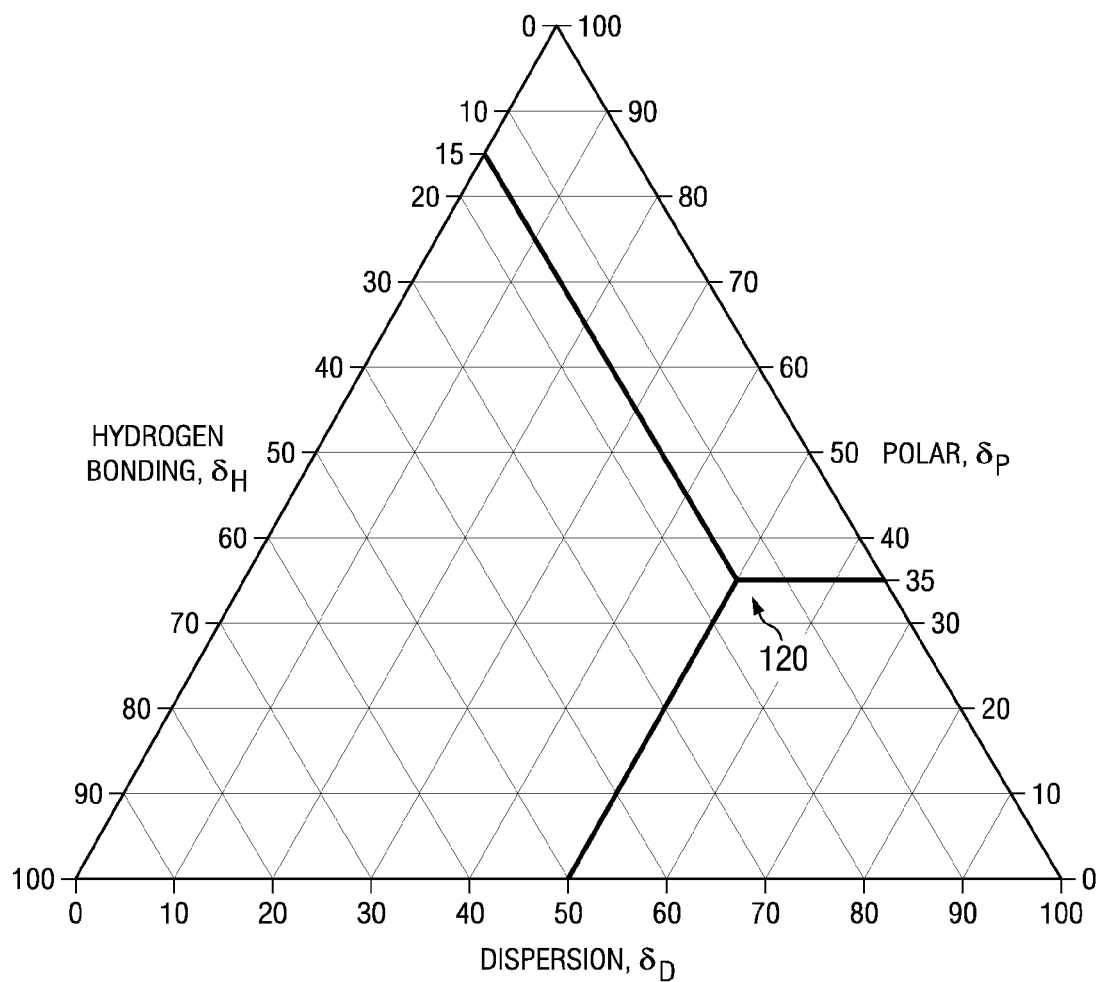
FIGS. 1 to 3 are Teas plots illustrating embodiments of the invention that provide a method for fabricating a cleaning solvent.

The format of a conventional Teas plot is illustrated in FIG. 1. The Teas plot has three axes corresponding to the dispersion ($\delta_D$), hydrogen bonding ($\delta_H$), and polar ($\delta_P$) parameters. The three parameters are scaled so that the sum of their values is 100 (or 1, depending on the convention). A hypothetical solvent represented by point 120 in FIG. 1 illustrates how the Teas plot is read. As shown by the bold lines in FIG. 1, point 120 represents a solvent having the parameter set: $\delta_D$=50, $\delta_H$=15, and $\delta_P$=35. A particular advantage of the Teas plot is its usefulness in predicting the solubility behavior of other solvents whose parameter set lies in a region near point 120.

Figure 2:
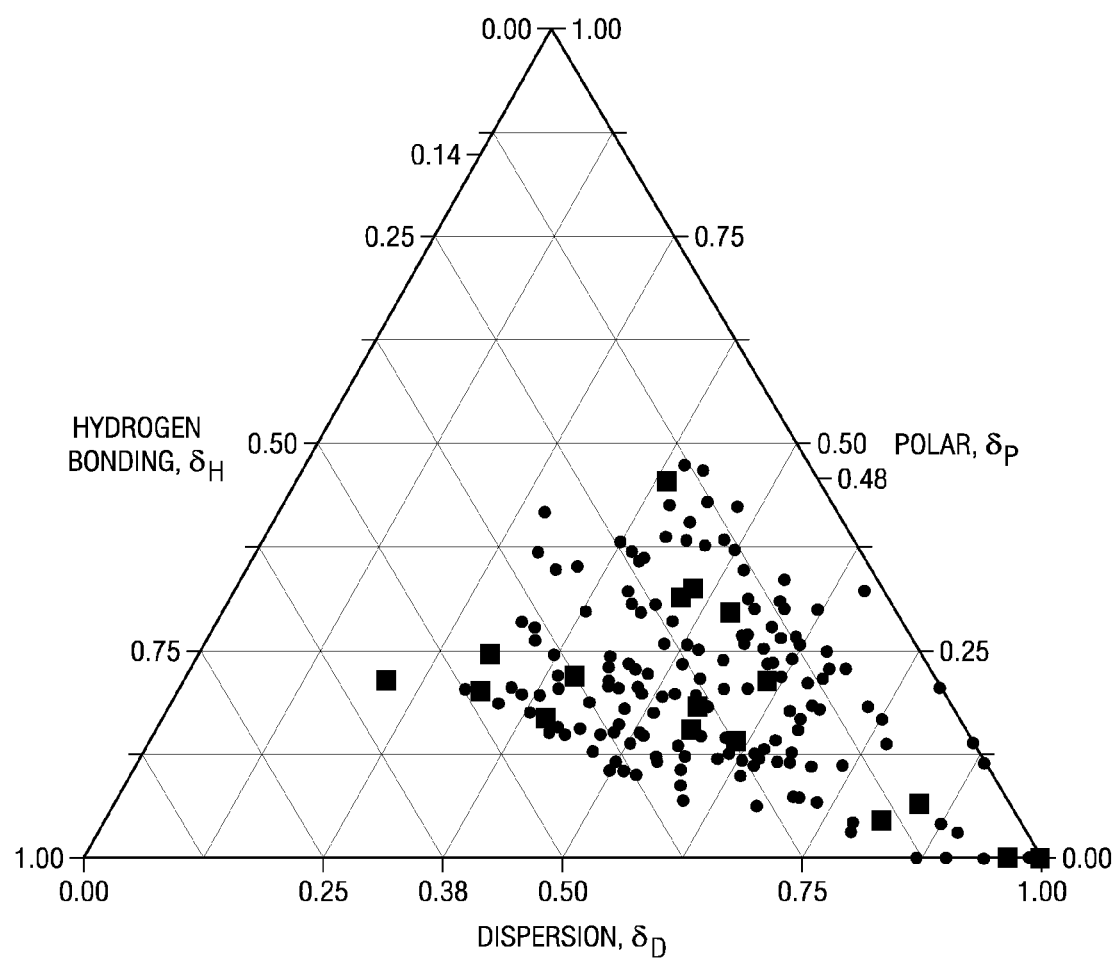

Turning now to FIG. 2, an illustrative embodiment of a method for manufacturing a semiconductor cleaning solvent comprises the following steps. The method includes selecting a small plurality of test solvents from large plurality of perspective solvents. The small plurality is preferably about 10 to about 20, although it may be smaller or larger. The large plurality is preferably larger than about 200, and more preferably larger than about 20,000. For ease of illustration, the exemplary large plurality is only about 100. In actuality, there are thousands of solvents for which the Hansen parameters are known. Since it is impossible to test several thousand cleaning solvents or their mixtures, a small plurality of solvents is selected from the large plurality of perspective solvents. The small plurality comprises test solvents that are used to develop a cleaning solution.

The equilibrium composition of a multi-component solution comprising the solute dissolved in the solvent is preferably described by a predetermined plurality of solubility parameters. In preferred embodiments, the plurality of parameters includes Hansen parameters and a Hansen radius of interaction. In preferred embodiments, a small plurality of test solvents is applied to solute samples and the degree of dissolution or swelling recorded. Based on the degree of dissolution or swelling, at least one solvent is selected from the large plurality of perspective solvents based on the Hansen parameters, thereby producing a new cleaning solvent.

In FIG. 2, solid squares represent the small plurality, and solid circles represent the large plurality. In preferred embodiments, the small plurality is selected such that its distribution of solubility properties is representative of the large plurality. The Hansen parameters of the solvents are known, but parameters for the solute are unknown. The manufacturing process begins by performing cleaning tests using the test solvents. On some samples, the test solvent will have no affect. Rarely, others will yield a positive result characterized by satisfactory dissolution of the material. With other samples, there will be an intermediate response characterized by swelling, or partial dissolution, of the solute.

Figure 3:
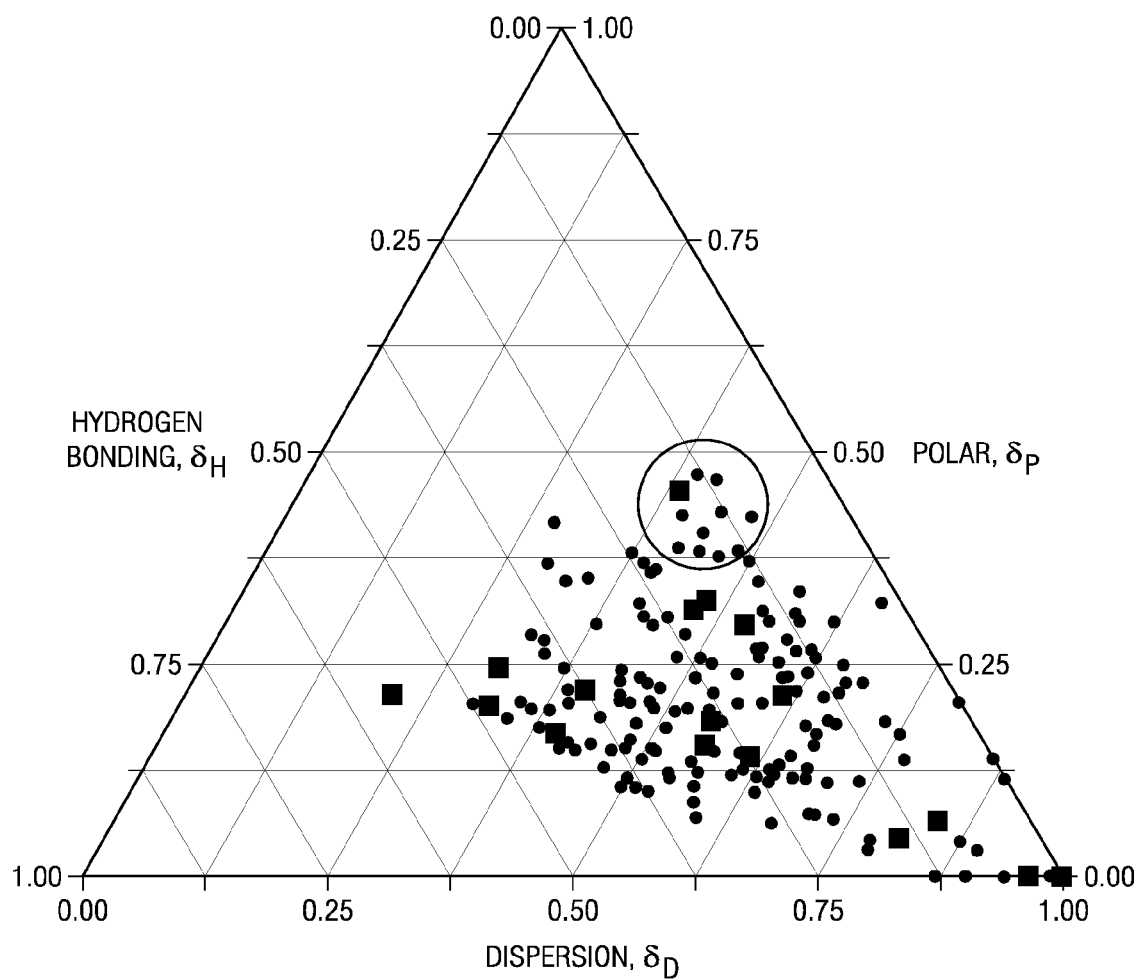

In a conventional method, even after finding that a given solvent causes swelling; a manufacturer is still faced with the daunting task of narrowing the field of perspective solvents. However, in preferred embodiments, the process is significantly improved. For example, consider the TEAS plot shown in FIG. 3. In FIG. 3, several solvents including one test solvent are circled. For illustrative purposes, assume that the test solvent is acetonitrile. As shown by FIG. 3, its solvent parameter set is approximately: $\delta_D$=38, $\delta_H$=14, and $\delta_P$=48.

One sees that there are only a few perspective solvents, which are circled, that are worth investigating. Advantages of embodiments are more clearly realized by recognizing that the number of perspective solvents are, from a practical manufacturing point of view, prohibitively large to fully examine. Selecting candidate testing solvents in view of their Hansen parameters rapidly streamlines the process.

Other embodiments dispense with the need for TEAS plotting by creating a computer database of perspective solvents. Selection of solvents based on test results may be done using conventional numerical methods, such as interpolation, Householder's method for linear systems, or Newton's method for nonlinear systems.

Embodiments may further include the calculation of Hansen parameters for mixtures of solvents. This embodiment is particularly advantageous when using a large computer database of solvents because the properties of a solution are frequently a nonlinear function of its individual components. Therefore, embodiments may include a numerical iterative process that includes the following steps. Based on the swelling test results, the desired Hansen parameters of the target solvent are obtained, for example by interpolating the Hansen parameters of the test solvents that yielded good results. If a solvent within the database has the target Hansen parameters, it is tested. If no suitable solvent exists, perhaps because of toxicity concerns, two or more solvents may be mixed. If the solvent is an ideal solution, the Hansen parameters of the mixture are accurately described by a linear combination of the individual components. If the solution is nonlinear, the Hansen parameters of the mixture may be more accurately approximated using a vapor-liquid equilibrium model available in the chemical arts.

In embodiments wherein the Hansen parameters of the solute are known, the target cleaning solvent composition may be calculated directly.

Embodiments described herein may be conveniently inserted into a semiconductor manufacturing process. For example, an unanticipated variation in the manufacturing process may occur, such as a temperature transient in a furnace. The temperature transient may produce a change in photoresist solubility, for example. Rather than scrap an entire run, embodiments herein enable the manufacturer to rapidly change photoresist strippers or even develop a new stripper to correct for the transient.

In alternative embodiments, the three-parameter Hansen solubility model is extended by an additional parameter to account for acidity or by an additional parameter to account for oxidizing or reducing agents. Since many solvents used in the semiconductor industry are non-aqueous, acid effects are more precisely described in embodiments using Lewis acid concentration rather than pH. Preferably, the acidity is calculated using $pK_a$ values, while a reducing/oxidizing (redox) parameter is measured in experiments or is calculated from redox potentials. A preferable method to adjust the solution redox potential includes adding hydrogen peroxide or peroxo-acetic acid. Embodiments including the redox potential are useful, for example, when solvent performance is influenced by its acidity, such as in oxidation.

Both pH (or Lewis acidity) and redox parameters are particularly useful in applications involving metals (e.g., copper) and their oxides. In certain instances, copper removal is preferred, for example to improve resistance in a via chain. In other instances copper loss is to be avoided. Cleaner selectivity evaluation may include placing a non-residue solute adjacent a residue and measuring an amount of non-residue dissolved by the test solvent.

In other embodiments of the invention, the three-parameter Hansen solubility model is extended by an additional parameter to account for surface tension or an additional parameter to account for viscosity. Such parameters are conveniently measured using conventional means. Embodiments comprising a viscosity solubility parameter are particularly useful when fluid convection is an important solvent consideration, such as in a flow-through bath. Embodiments comprising the surface tension solubility parameter are particularly useful when good wetting is important. In other embodiments, the surface tension solubility parameter may be expressed using the contact angle, a measurable quantity. In alternate embodiments, the surface tension of the cleaner may be adjusted using surfactants, which affect surface behavior without significantly changing bulk chemical properties.

In still other embodiments, the solubility model includes a fluoride activity parameter and/or an etch rate solubility parameter. The fluoride activity parameter may be calculated from concentrated fluoride sources, activity, and solubility data. The fluoride activity parameter is particularly useful in combination with the etch rate parameter. Therefore, the fluoride activity parameter and etch rate parameter may be combined into a single parameter or further broken down into sub-parameters that account for temperature changes or deviations from standardized conditions.

Sometimes a good solvent may not be readily available. For example, a good solvent might be highly carcinogenic. Therefore, preferred embodiments solve this problem by adjusting the temperature of the solution, generally a temperature increase. Gaps between suitable parameters could be overcome by the increase in temperature. Embodiments including a temperature adjustment advantageously increase the three dimensional sphere of solubility. This causes a larger set of perspective solvents to lie within this sphere.

As noted above, there are other solubility models than the Hansen model. Another embodiment of the invention includes a solubility model based on the surface free energy of the solute. A basic requirement shared by all liquid cleaning methods is that the cleaning solvent must at least partially wet a surface of the solute. The parameters known to control wettability include the solvent's surface tension, its contact angle with the surface, and the properties of the surface. A particularly relevant surface property is its surface free energy. An embodiment of the invention includes characterizing the solute surface free energy using liquids having a known surface tension.

An embodiment includes measuring the contact angle between at least two solvents and the solute to be cleaned. The surface tension of the solvents is preferably described in terms of a combination of a polar and dispersive component. The two components of the surface free energy model may share a similar theoretical foundation as the analogous parameters in the Hansen solubility model; however, their values are generally not equal and are not to be confused.

The contact angle between a solvent having a known surface tension and the solute is measured using conventional techniques. The data for several points are plotted using a surface free energy plot. For each contact angle measurement, a point in the plot is generated. The y-coordinate is provided by the formula $y=\{(1+\cos(\theta))/(2\sigma_l\sqrt{\sigma_l^d})\}$ and the x-coordinate is provided by $x=\sqrt{\sigma_l^p/\sigma_l^d}$, which is a constant for each tested solvent. Therefore, the tested liquids should be as different as possible in the $\sigma_l^p/\sigma_l^d$ ratio. The surface free energy of the solute is found using the slope and y-intercept: $A=\sqrt{\sigma_s^p}$ and $B=\sqrt{\sigma_s^d}$, wherein the polar and dispersive component of the surface free energy are $\sigma_s^p$ and $\sigma_s^d$, respectively.

The total free energy of the surface is the sum of the polar and dispersive components. Having determined the polar and dispersive components according to embodiments provided herein, an optimum cleaner is selected by matching the polar and dispersive components of the solvent to the solute. For this purpose based on the known free surface energy of the surface and the surface tension of the liquid (both in dispersive and polar part), a potential contact angle may be calculated. Its value is preferably in the region between about 10 and 40 degrees.

In other embodiments, a customized cleaning solution is developed by blending a plurality of solvents. Preferably, the blending includes combining solvents having known solubility parameters. The solubility parameters of the resulting blend may be predicted based on the mole fraction of the individual solvents comprising the combination. Embodiments may include blending or adding materials not normally considered solvents, like salts, for example.

In summary, solvent selection comprises the following steps. A plurality of test cleaning solutions having known solubility parameters is selected. The solubility parameter of multi-component cleaning solutions may be calculated using the molar fraction of the components. The material to be removed, i.e., dissolved, is treated with different chemicals or mixtures of known Hansen parameters.

In photoresist removal, for example, cleaning effectiveness is evaluated by characterizing the amount of photoresist swelling in a given time. On some samples, the solvent will have no affect. Others will yield a positive result characterized by dissolution of the material. With other samples, there will be an intermediate response characterized by swelling of the solute. In systems with poor or intermediate results, the solubility sphere may be adjusted by raising the temperature, adding an oxidizing or reducing agent, adjusting the fluoride content, or adding a surfactant to change surface tension, for example.

By localizing the solvent testing domain, multiple solutions, may rapidly be investigated and the composition of a target cleaning solvent calculated using suitable numerical methods. Solutions or blends of solvents can be calculated to circumvent toxicity, unavailability, environmental or other critical issues of some chemicals, by molecular fraction and individual parameter sets. The solution could be fortified by improving the availability of Lewis acids and bases or the oxidizing capabilities. Other chemical/physical properties like viscosity, surface tension, etc., could be modified by exchanging chemicals, yet still keeping the desired parameter set in focus.

Embodiments described herein have other applications that do not involve comparing chemicals for cleaning solutions. One such application includes semiconductor manufacturing involving low-k dielectrics.

Low-k dielectrics are an important component in many semiconductor devices. Since air has a dielectric constant of about 1, one method for making low-k dielectrics incorporates air into dense materials to make them porous. The dielectric constant of the resulting porous material is combination of the dielectric constant of air and the dielectric constant of the dense material. One way of making porous dielectrics is to include a pore generating material (a porogen) in a low-k dielectric. At a suitable stage in device manufacture, dielectric pores are generated, usually by thermal degradation of the porogen.

There are two processing routes commonly used in low-k dielectric manufacture. These are frequently referred to as the solid first route and the porous first route. Both routes are commonly used in the dual damascene process, for example. In the porous first route, the dielectric is deposited and made porous before the dual damascene trenches and vias are patterned and copper filled. In the solid first route, the dielectric is deposited, patterned, copper filled, and then made porous. An important consideration for selecting one route over the other is potential contamination of the pores with pore generation byproducts, which degrade the low-k dielectric. Another consideration is the higher surface area of porous material and the increased risks of surface contamination or damage.

Using embodiments described herein, Hansen, redox, etching, surface tension and other parameters guide the decision as to which pore generation route to take. For example, the pore generation process may include chemical extraction of the porogen from the dielectric matrix. Comparison of the solubility parameters for the solvent, the porogen, and the dielectric matrix will determine whether one or another component is sensitive to chemical attachment, such as oxidation/reduction, or acid/base reactions.

Embodiments of the invention described above may be included in solvent evaporation or drying processes. For example, in a solvent drying step, a mass loss vs. temperature plot may characterize the amount and properties of the unevaporated material. For example, if after using the highest possible drying temperature, a residue remains, a solvent or cleaner provided by embodiments provided herein may remove the residue. Information about boiling or evaporation behavior may be included in a database of mass loss, temperature, and/or other parameters like surface tension. Such information may be used to estimate the composition in a spinning process or in open storage over time.

Although the present invention and its advantages have been described in detail, it should be understood that various changes, substitutions and alterations may be made herein without departing from the spirit and scope of the invention as defined by the appended claims. For example, it will be readily understood by those skilled in the art that materials and methods may be varied while remaining within the scope of the present invention. It is also appreciated that the present invention provides many applicable inventive concepts other than the specific contexts used to illustrate preferred embodiments. Accordingly, the appended claims are intended to include within their scope such processes, machines, manufacture, compositions of matter, means, methods, or steps.

What is claimed is:

1. A method for fabricating a semiconductor device, the method comprising:
   generating a material on a semiconductor substrate;
   removing the material with a cleaning solution comprising a solvent, wherein the solvent is selected according to a selection method, the selection method comprising
      selecting a small plurality of candidate solvents from a large plurality of perspective solvents, wherein each member of the small plurality of candidate solvents has a known solubility parameter;
      measuring an amount of swelling caused by each member of the small plurality of candidate solvents using a test sample of the material;
      calculating solute solubility parameters for the material by combining solubility parameters of the small plurality of candidate solvents in proportion to the amount of swelling of the test samples of the material; and
      selecting the solvent from the large plurality of perspective solvents based on the solute solubility parameters for the material.

2. The method of claim 1, wherein selecting the solvent comprises mixing two solvents from the large plurality of perspective solvents forming a mixture so that solubility parameters for the mixture approximate the solute solubility parameters for the material.

3. The method of claim 1, further comprising adjusting at least one of a temperature, a surface tension, a redox potential, an acid content, a viscosity, and a fluoride concentration of the cleaning solution.

4. The method of claim 1, wherein calculating the solute solubility parameters of the cleaning solution includes using a Hansen solubility model.

5. The method of claim 4, wherein the Hansen solubility model includes a parameter describing acidity of the solvent.

6. The method of claim 4, wherein the Hansen solubility model includes a parameter describing redox potential of the solvent.

7. The method of claim 4, wherein the Hansen solubility model includes a parameter describing a temperature of the solvent.

8. The method of claim 4, wherein the Hansen solubility model includes a parameter to account for surface tension of the solvent.

9. The method of claim 4, wherein the Hansen solubility model includes a parameter to account for viscosity of the solvent.

10. The method of claim 4, wherein the Hansen solubility model includes a fluoride concentration of the solvent.

11. The method of claim 4, wherein the Hansen solubility model includes an etch rate of the solvent.

12. The method of claim 1, wherein the material comprises a low-k dielectric.

13. The method of claim 1, wherein the material comprises a metal.

14. The method of claim 1, wherein the material comprises a metal oxide.

15. The method of claim 1, wherein the material comprises a resist.

16. The method of claim 2, wherein mixing the solvent comprises approximating the solvent by applying a vapor-liquid equilibrium model.

17. The method of claim 1, wherein selecting the solvent comprises mixing three or more solvents from the large plurality of perspective solvents forming a mixture so that solubility parameters for the mixture approximate the solute solubility parameters for the material.

18. The method of claim 1, wherein the small plurality of candidate solvents is about 10 to about 20 and the large plurality of perspective solvents is larger than about 200.

19. The method of claim 1, wherein the small plurality of candidate solvents is about 10 to about 20 and the large plurality of perspective solvents is larger than about 20,000.

* * * * *